United States Patent [19]

Van Dorn

[11] Patent Number: 4,653,314

[45] Date of Patent: Mar. 31, 1987

[54] ARTICLE AND METHOD HAVING SUBSURFACE PROPERTY GRADIENT DETERMINATION CAPABILITY

[76] Inventor: Horace B. Van Dorn, 51 Chatham Rd., Kensington, Conn. 06037

[21] Appl. No.: 659,716

[22] Filed: Oct. 11, 1984

[51] Int. Cl.⁴ ............................................. G01N 3/00
[52] U.S. Cl. ........................................ 73/78; 148/128
[58] Field of Search ............ 73/78, 81, 150 R, 432 Z; 148/128, 129

[56] References Cited

U.S. PATENT DOCUMENTS 4,235,018  11/1980  Saberg ............................ 73/150 R
4,510,798  3/1985  Prussin ............................. 73/150 R

FOREIGN PATENT DOCUMENTS 214865  6/1968  U.S.S.R. ................................. 73/78
414321  5/1974  U.S.S.R. ............................. 148/128
441472  12/1974  U.S.S.R. ................................. 73/78

Primary Examiner—Jerry W. Myracle
Attorney, Agent, or Firm—McCormick, Paulding & Huber

[57] ABSTRACT

An annular bead or other protuberance is provided on the outside of a bearing or other part on a non-critical surface so that the protuberance can be case hardened in the same manner as critical surfaces of the part and provide a degree of hardness at each surface that exceeds the hardness at predetermined depths below that surface. The shape of the protuberance is chosen to permit quantitative testing for hardness depth and hardness gradient. The bead or protuberance is then removed so as to expose at a scar the resulting subsurface structure or property gradient for inspection. Hardness inspection can be utilized to provide Rockwell C hardness indications at spaced points along the scar.

18 Claims, 18 Drawing Figures

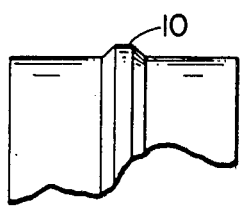
FIG. 7
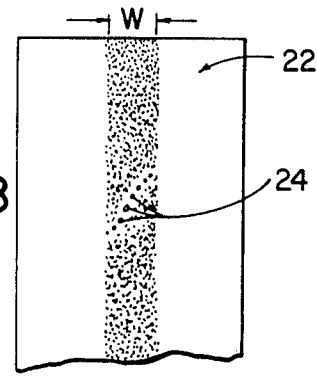
FIG. 8
FIG. 9
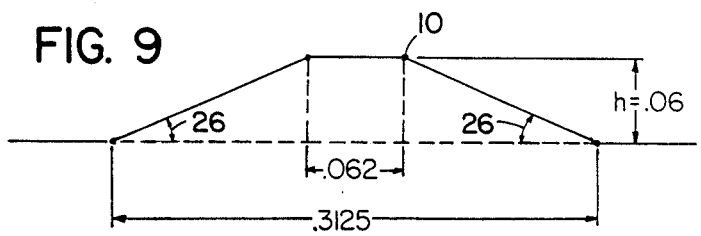
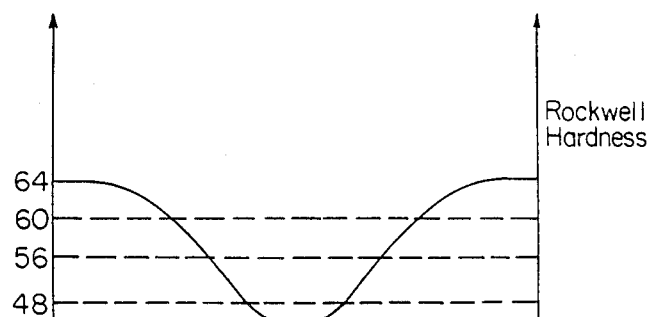
FIG. 10

ARTICLE AND METHOD HAVING SUBSURFACE PROPERTY GRADIENT DETERMINATION CAPABILITY

BACKGROUND

This invention relates generally to a method for determining subsurface gradient characteristics of articles and deals more particularly with a system for the quantitative determination of hardness at sub-surface depths in operational components such as a jet engine bearing parts. More specifically this disclosure deals with non-destructive measurement of the hardness existing at calibrated depths below the surface of a body.

In today's aircraft gas turbine engines, bearings operate at speeds in the range of 1.8 to 2.0 million dN where d equals the inner ring bore diameter of the bearing in millimeters and N equals the shaft revolutions per minute. Future generation ball and roller bearings are now in the design and testing stage for operation at 3 million dN and higher, where engine efficiency is exponentially improved. At higher N speeds, greatly increased centrifugal forces are imposed upon the bearing raceways by the orbiting rolling elements. These radial forces not only substantially reduce the margin of bearing capacity available for supporting operational thrust, radial and overturning moment loads of the engine but also produce hoop tension in the constraining bearing outer rings. Other significant hoop tension stresses develop in the inner ring due to exposure to its own centrifugal environment, while the usual heavy press fit of the inner ring on the shaft creates additive hoop stress. In the case of multiple concentric engine shafts both inner and outer rings of intermediate position bearings experience centrifugal hoop stress as they each rotate at their own rates. From whatever source, tensile stresses promote crack initiation and propagation.

As engines become larger and concentric shafts prevail, bearing diameter, the d factor, increases and the d N challenge agains becomes more severe.

Engine thrust to weight ratios and space restrictions are improved when rolling contact bearings are designed to serve structural functions such as to eliminate the need for housings, baffles and bulkheads. In this role many bearing designs now feature flanges, scallops, bolt-holes, oil passages, seal grooves, or other geometric anomalies which introduce unusual bending and stress raising characteristics. These circumstances also promote crack initiation and propagation in today's high hardness brittle bearing materials.

Extensive testing has proven that today's through-hardened steel main shaft ball and roller bearings with all these newly required features have not been able to perform reliably above the 2.0 million dN barrier. Minor rolling contact fatigue cracks which may typically occur in the raceways of the relatively brittle high hardness steel tend to propagate at an alarming rate as a result of the stress raising design or externally applied structural loads, sometimes proceeding to sudden and unexpected catastrophic failure. A materials change must be made.

Recent bearing material research has shown that case-hardened low carbon tool steel can provide both the tough cores for structural strength and "crack-stopper" requirements and the high hardness surfaces for best rolling contact fatigue, wear and penetration resistance. The usual alloys, molybdenum, manganese, chromium, vanadium, etc., are selectively added to provide the hardenability, hot-hardness, dimensional stability, carbon absorption and corrosion resistance as appropriate.

Low carbon M50 or matrix alloy steels have been selected for the new bearings and when combined with rather conventional carburizing processes have proven in full scale tests to serve these multiple requirements. It is doubtful however that these case-hardened parts dare be flown in aircraft until some reliable method such as described herein is adopted to assure the air-worthiness of the otherwise hidden hard case characteristics.

Carbon enrichment of the surface and near-surface volume of an article, and subsequent preferential hardening so as to provide a hardening gradient is old in the art, but accurate non-destructive measurement of property gradient from surface to core and the depth of the hardened zone, presents a new challenge. It becomes most important in critical production manufacture that means be provided to analyze the physical properties through the subsurface transition zone and into the core. Destructive sampling inspection procedures do not insure the integrity of every kindred part. It would be of great advantage over present methods to be able to carry out this analysis precisely on each final part by a non-destructive testing method to qualify it for service in any highly critical application.

A general object of the present invention, then, is to provide a system which will assure that the hardness character of the surface, subsurface, and core meet the standards referred to previously. More particularly in the jet engine bearing environment the depth to which case hardening is achieved must not be so thick as to permit cracks to progress and lead to relatively sudden failure of the part, nor may this case hardening be so shallow as to lead to early spalling and too frequent bearing replacement requirements. As a result of utilizing the method and means described herein, the suitability of the material at all levels, surface and below, is insured for the rigors of performance.

SUMMARY OF THE INVENTION

In carrying out the method, the present invention contemplates a system for producing an article that can be nondestructively tested for a physical or chemical property, preferably a property exhibiting a gradient relative to the depth beneath some active or working surface of the article. A typical such property of particular concern in jet engine bearings, for example, is hardness as now measured on the "Rockwell C" hardness scale. However, in addition to hardness, other properties of this general type may be tested by other testing techniques in accordance with the system of the present invention, and such system can be summarized as follows.

The first step in carrying out the method of the present invention is to form the article to a desired shape, which shape has several surfaces, some of which surfaces are critically contoured as dictated by desired requirements. Such a critically contoured surface might be the bearing running surface itself in a typical ball bearing raceway. Other of such surfaces are not so critical, and a non-critical surface might be the outer surface if the inner surface defines the bearing raceway or vice versa.

Another step is providing a raised portion, preferably in the form of an annular bead on at least one such non-critical surface if the article is a bearing ring. The article is then subjected to the surface treatment process, so that said critical and non-critical surfaces are commonly altered in some physical or chemical property, for example, in hardness and the inherent brittleness associated therewith.

The raised portion so defined on a non critical surface is available for removal in the normally provided forming operations, after surface treatment. The resulting surface left as a result of removing the raised portion exposes in a calibrated array the surface and sub-surface properties for examination.

In order to more particularly define the depth to which the surface has been so altered, the raised removal portion of a non critical surface is preferably contoured to a particular cross sectional shape. A trapezoidal shape may be provided to facilitate displaying the gradient being checked. Such a trapezoidal form will ultimately permit a laterally spaced series or Rockwell hardness tests to be made transversely across the scar of the removal portion, with the result that one can readily ascertain the depth to which carbon has penetrated and the hardness has been obtained in the treating steps. It should be noted, however, that the shape of the raised removal portion can be chosen to meet specific design requirements, and that the trapezoidal shape referred to may be preferred but is not essential to the present invention. For example, an annular bead of convex or other configuration may be simpler or more suited to inspection of a property gradient that is not linear. Removal of the raised portion or bead in final processing not only leaves the permanently displayed spectrum of subsurface characteristics on the non-critical surface, but does so without requiring any change in the geometry of the finished part.

BRIEF DESCRIPTION OF THE DRAWINGS

FIG. 7 is a partial view of the bearing ring shown in FIG. 1.

FIG. 8 is a view of the same bearing ring depicted in FIG. 7 with the annular bead ground away, and with Rockwell hardness impressions provided in a transversely extending line across the scar of this ground off bead.

FIG. 9 is an enlarged view of the bearing bead of FIG. 7 prior to the grinding operation and depicts the the trapezoidal shape of the bead in detail.

FIG. 10 illustrates graphically the results of the Rockwell hardness tests taken transversely across the bead scar area after the bead had been ground away.

DESCRIPTION OF THE PREFERRED EMBODIMENTS

Figure 1:
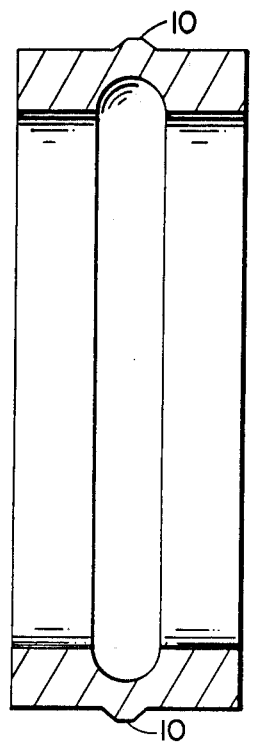
FIG. 1 is a vertical section through a ball bearing outer ring equipped with a raised portion or annular bead in accordance with the present invention.
Figure 2:
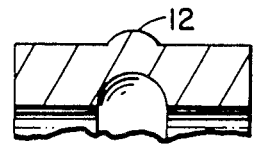
FIG. 2 is a partial sectional view of one side of another bearing outer ring with a slightly different bead configuration.
Figure 3:
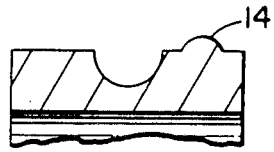
FIG. 3 is a partial sectional view of a bearing inner ring with an annular bead provided adjacent to the bearing surface.
Figure 4:
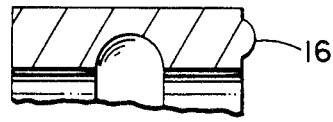
FIG. 4 is a partial sectional view of another bearing inner ring with the bead provided on an outer face of the ring.
Figure 5:
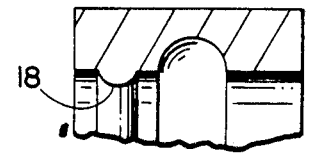
FIG. 5 is a partial sectional view of a bearing outer ring with an annular bead provided adjacent to the surface itself.
Figure 1A:
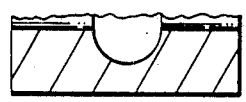
FIG. 1A is a partial sectional view through the outer ring of FIG. 1 after the bead has been ground away.
Figure 6:
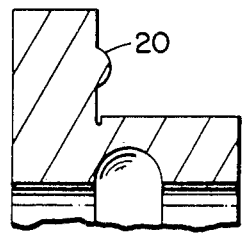
FIG. 6 is a sectional view showing a portion of an outer ring with a radially outwardly extending flange having an annular bead provided on the flange.
Figure 11:
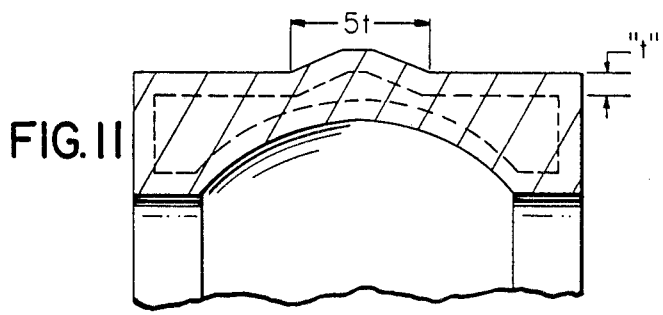
FIG. 11 is a graphical representation of a typical bearing ring with the "case" portion illustrated relative to the "core" as would be the situation after heat treatment and case hardening.

In testing for hardness gradient of carburized parts in the past, it has been necessary to sacrifice an expensive kindred element or dissect a sample slug or cadaver which hopefully has the same historical processing and material pedigree as the parts to be used. In the prior testing methods, the condition of the intended useful part is not actually measured, but is inferred from the sample or sacrificed part. Moreover, sample cadavers and their test results often must be held for long periods of time in a museum and bookkeeping systems where mix-ups or loss can occur. Costly and bothersome coding practices have been necessary.

The non-destructive testing method to be described provides the same advantages as the destructive testing method without its associated disadvantages. It involves a peculiar design feature of the body itself which feature disappears from the finished part as a result of following the method or procedure to be described.

In carrying out my improved method, a bearing ring, gear or other part, is provided with a protuberance of modest dimensions so that material cost and metal removal expenses are not incurred.

In its simplest form, the protuberances on a bearing ring are illustrated in cross sectional in views in FIGS. 1 through 6, inclusive. These views illustrate suitable locations for an annular protuberance, bead or raised portion 10, 12, 14, 16, 18, and 20 respectively such as might be used for either an inner or an outer bearing ring.

Such bearing rings are subjected to carburizing and heat treatment in accordance with appropriate practice. Thus, the protuberance is subjected to the same surface treatment as the working surface of the part itself. The protuberance is ground down which leaves a smooth surface and scar area with a hardness gradient across the area ranging from a maximum degree of hardness on either side of the scar (where the annular bead was) to a minimum at the center of the area where core material appears at the surface. This is well illustrated in FIGS. 8, 9 and 10 where, in the latter view, it is clearly shown that the degrees of hardness is related to the lateral dimension or "virtual depth".

It is an important feature of the present invention that the protuberance be designed to suit an expected gradient of hardness relative to depth which is regarded by the designer to be normal or desired. The shape of the annular bead is chosen to yield a spread of hardness across the bead corresponding to a predetermined gradient into the core and should provide enough work area for the inspection method applied.

Referring now to FIG. 7 in greater detail, the method of the present invention as disclosed, comprises forming the bearing ring with a raised portion 10 that is then ground down to provide a smooth external appearance as indicated generally by the arrow 22 in FIG. 8. A scar area shown by the stippled pattern is created at a known dimensional location, and visible differences appear in the surface finish corresponding to the hard and soft areas. The range of hardness across this scar area, can be quantified by utilizing a Rockwell hardness tester to make the impressions illustrated at 24. These impressions, also provide a visual indication of hardness. The annular distribution of the hardness in the scar area in terms of Rockwell C hardness numbers is depicted graphically in FIG. 10 which can be compared with the initial configuration of the protuberance or bead shown in FIG. 9 with the same horizontal scale. At the center of the bead area, the lowest hardness reading is obtained (46 RC in FIG. 10) and at the margins of the bead area the highest Rockwell hardness numbers are obtained (64 RC in FIG. 10). A generally sinusoidally shaped hardness gradient is obtained in between. For purposes of definition hereafter, case depth t is given as the full depth of hardness change due to the presence of absorbed carbon in the treated part.

For a desired or normally expected case depth of t=0.050, "a bead height 20% greater, i.e. h=0.060 inch in FIG. 9, is selected to make sure the center of the bead scar will reveal core material on the finished surface. Bead cross-section is a symmetrical trapezoid in this example and has an overall width of 0.3125", a centered land of 0.062 inch. This calculates out to a side slope angle 26 of 25.6°. The projected scar area then is large enough for a series of Rockwell C diamond impressions 24 on a diagonal path as shown in FIG. 8. The overall width of a symmetrical bead should typically be a minimum of five times the intended depth of hard case.

For case depth measurement and examination by this method it is desirable to add or subtract any difference in hard stock removal between the test surface and the finished running surface of the examined part. This difference is normally only a few thousandths of an inch for precision parts, and maybe negligible in certain instances.

By this method, case and core evidence is permanently carried on the part itself for easy verification at any time in the future. Hence the method provides protection against loss of cadaver samples or test records.

Figure 12:
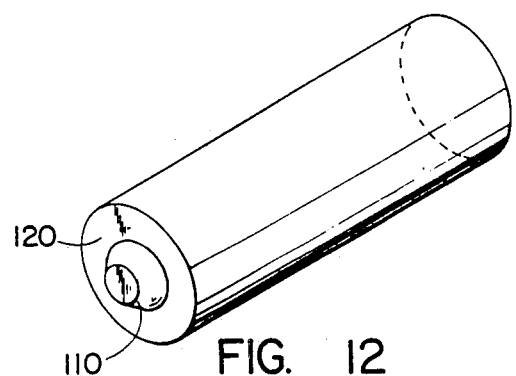
FIG. 12 is a perspective view of a cylindrical roller having a shaped protuberance at one end to permit treatment thereof in accordance with the present invention.

While FIGS. 1 through 6 illustrate different locations for the annular bead provided on inner and outer bearing rings, it will be apparent that other raised portions may be provided on other parts with the same result. For example, where rollers for bearings are to be tested by this invention, at least one end portion may be provided with a raised land as illustrated at 110 in FIG. 12. If this land is ground away after heat treatment, one is left with core material near or at the surface 120 and one can test for and provide a permanent record of hardness gradient for the roller in the same fashion as obtained for the bearing ring of FIG. 1. Furthermore, although the present invention is described with reference to bearings, particularly those adapted for use in state-of-the-art jet engines, it will be apparent that the invention can also be adapted for use in the fabrication of other parts such as rotating seals, gears for transmissions, and other case hardened products.

Figure 13:
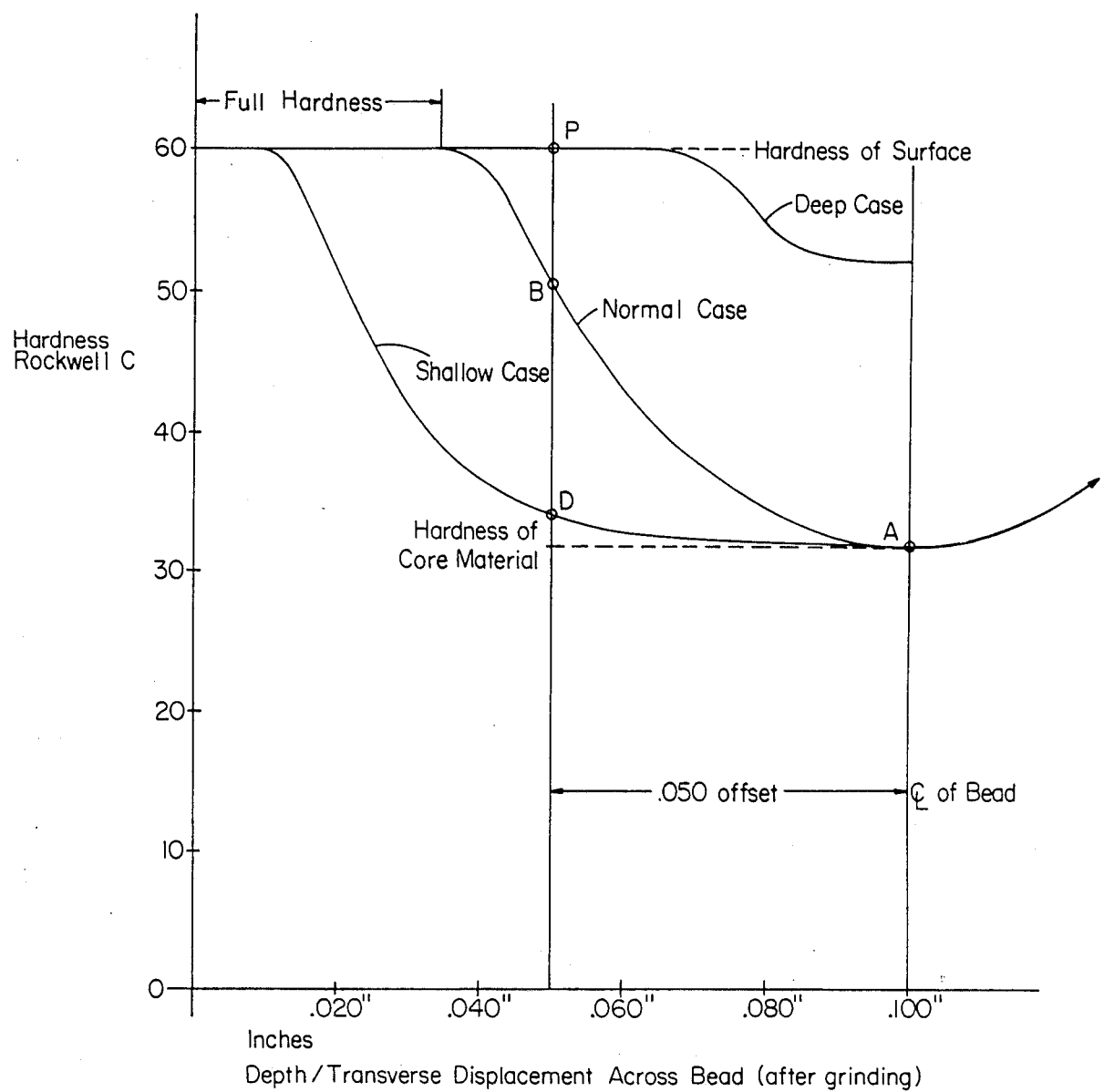
FIG. 13 is a graphic representation of hardness versus depth across the bead scar for several different surface treatments.

FIG. 13 shows several typical hardness patterns of the type in FIG. 9 for bearing rings fabricated, heat treated, case hardened, finish ground, and subsequently subjected to hardness testing with a conventional Rockwell type apparatus in accordance with the present invention. The curve labelled "normal case" shows the surface hardness is 60 RC and the depth of this hardness, the full hardness, extends approximately 0.035 inch below the surface. The core hardness is 32 RC at 0.100 inch with a sinusoidal gradient displayed between the hard case and the core. The curves labelled "shallow case" and "deep case38 show different degrees of hardness at various depths and reveal that the annular bead provided on the bearing ring should be shaped and dimensioned so as to yield a desired pattern of displayed hardness gradient on the finished part. If the desired case depth is chosen to be more shallow as illustrated by the "deep case" gradient, one might choose a lower bead height and lower side angles. On the other hand, if the desired case is chosen to be deeper, the bead height would be greater and side angles steeper for the same breadth of display. Selection of side angle and overall width of the bead is a function of the space needed or available for measurements.

Thus, the designer should determine what amounts to a normal pattern for the gradient in a particular part and an optimum cross sectional shape can be chosen for the bead as outlined above. Thus, the hardness gradient can be associated directly with the cross sectional configuration of the bead in a particular article to be treated.

After the bead has been ground off the external surface of a bearing ring, such as shown in FIG. 8 for example, hardness readings can be taken along two or more transverse lines which are circumferentially spaced around the ring and then compared one to another to heighten the accuracy of the resulting measurements or to check eccentricity of case depth.

It is possible to check for expected case depth taking only three readings, or only two if the surface hardness has previously been verified by in-process heat treatment inspection. One reading at the centerline of a bead scar establishes core hardness. A second or offset reading taken half way toward the lateral test area boundary establishes an intermediate hardness value on the gradient slope. For example in FIG. 13 the "normal" gradient line shows the core value at point A is 32 RC; and at 0.050" offset, point B, a hardness of 50 RC. A piece part with these values is acceptable. Too shallow a hard case would show a 32 RC value at the 0.050" offset, point D. Too deep a case would give a reading of 60 RC at the offset point P for example. Both of the latter values signal rejection of the part.

Although the above described invention has been closely tied to the current Rockwell hardness testing system utilizing conventional diamond penetration methods to define and quantify this "hardness" parameter, the invention is not so limited, and other hardness or property quantification systems might be used within the scope of the present invention. For instance, other testing methods might include some degree of chemical etching to enhance inspection by the naked eye. A probe utilizing electromagnetic energy might also be adapted for use in testing for properties. X-ray defraction scanning is another alternative. Molecular resonance or any other inspection could also be adapted in testing for one or more properties of the type to which the present invention can be directed.

The present invention provides a convenient system for determining internal hardness in rolling contact bearings of the type used in present day and future jet engines. Other products can be similarly tested such as bearings for other applications and transmission gears. The invention also provides a convenient method for testing recut or reground bearings for safe values of residual case hardening. The value of the original case thickness can be obtained from the part by reinspection of the non-critical scar surface then be corrected for the depth of the case in the critical surface.

In lieu of actual hardness testing, one could conceiveably determine from a visual inspection with or without etching, whether or not an article has met certain minimum requirements. If the hard case is shallow this fact will reveal itself without etching because the core material will be exposed in a wider portion of the bead scar than would be true for proper case hardening. At least, the error of substituting wrong material would be obvious to the viewer. In short, the present invention in its broadest aspect might be utilized in a go/no-go method of inspection for the part itself.

Figure 14:
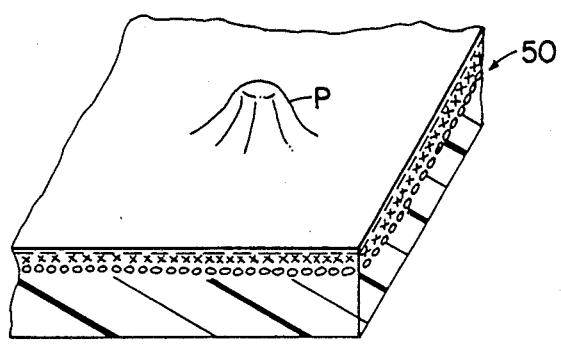
FIG. 14 is a perspective view of a composite material made up from several layers and bound in a resinous matrix.
Figure 14A:
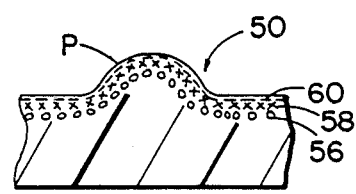
FIG. 14A is a vertical section through the protuberance in FIG. 14.
Figure 15:
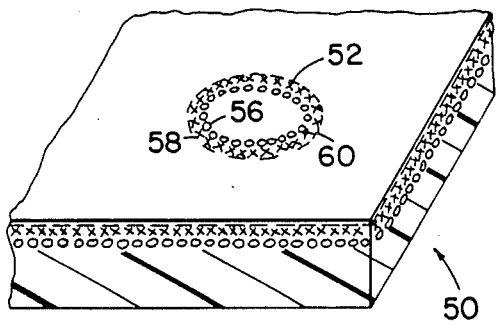
FIG. 15 is a view similar to FIG. 14 but with the protuberance cut away.
Figure 15A:
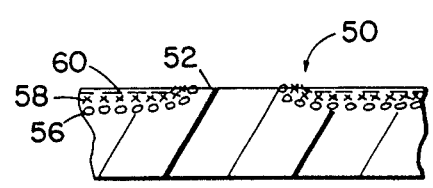
FIG. 15A is a vertical section through the FIG. 15 material where the protuberance is cut away.

Although the above described invention has been presented in terms related specifically to the inspection of steel, other materials might be adapted for use with this testing technique. For example, plastic composite materials prepared in stratified layup form for molding, or as pressed in precuring processes, can be analyzed. In FIGS. 14 and 14A the article 50 is prepared from a base 54 of plastic or epoxy resin in which a layer 56 of cotton cloth is embedded and covered with wire screeing 58. The screening is then overlaid with a polytetrafluoroethylene cloth 60 and the whole structure is secured by the resin. The composite is made up, cured, and shaped to final dimension with a protuberance P. The protuberance is provided integrally in the body as a sacrificial portion that can be removed as in FIGS. 15 and 15A for subsequent inspection of subsurface structure in the article. If a simple dimple was provided on the part, a sort of vaccination scar 52 will result from the removal. If a rib is provided on a circular part as in the steel bearing ring described above, an annular pattern will appear. The composition structure of the article is revealed in a "contour line" configuration once the protuberance or bead has been removed. This might be produced for decorative art or for electrical or electrostatic purposes where a conductive layer or layers are locally exposed.

In its broadest application, the present invention can be best described as comprising a series of steps which include; first, producing the article such that it exhibits a designed in gradient relative to the distance from the surface of some physical or chemical property. Although hardness is the property described in greatest detail hereinabove other properties might be exposed for testing in accordance with the present invention. The article is formed to a desired shape with several surfaces, some of which surfaces are critically contoured as dictated by design requirements. Other surfaces are not critical as to such design requirements but are so configured that they exhibit a gradient of the property to be measured relative to the distance from the surface of the body. A raised portion of the body is provided in at least one such non-critical surface and in the case of steel hardening the body is subjected to a surface treatment such that at least some of these critical areas are altered in some physical or chemical property (carbon content and hardness) along with the non-critical surface. This assures that the raised portion is available for subsequent processing. The subsequent processing removes the raised portion as by grinding to conform the entire outer surface of a part to its final form, and then testing can be accomplished, for example, by Rockwell hardness techniques, to provide an indication of the property gradient and depth of change across the scar area where the raised portion has been at least partially ground away.

I claim:

1. A method for producing a body which can be tested for a physical or chemical property that exhibits a gradient relative to the distance below the surface of said body, said method comprising:
  (a) forming the body to a desired shape with several surfaces, some of which are critically contoured as dictated by design requirements, and some of which are non-critical,
  (b) providing a raised portion on at least one such non-critical surface,
  (c) subjecting the body to a surface treatment process such that at least some of said critical surfaces are altered in one or more such properties and so that said at least one non-critical surface is similarly altered, whereby said raised portion is available for testing.

2. The method of claim 1 wherein the step of providing a raised portion on said non-critical surface more particularly comprises shaping said raised portion so that its cross sectional shape provides different heights relative to the non-critical surface itself.

3. The method of claim 2 further characterized by the additional step of removing said raised portion after treating said body in accordance with step (c).

4. The method of claim 3 further characterized by the additional step of inspecting the surface after said removal step to ascertain the depth to which the surface properties have been altered by the treating step (c).

5. The method of claim 4 further characterized by the additional step of utilizing said body pursuant to its designed-in requirements.

6. The method of claim 3 further characterized by the additional step of utilizing said body pursuant to its designed-in requirements.

7. The method of claim 1 further characterized by the additional step of removing at least some of said raised portion after treating said body in accordance with step (c).

8. The method of claim 7 further characterized by the additional step of inspecting the surface after said removal step to ascertain the depth to which the surface properties have been altered by the treating step (c).

9. The method of claim 8 further characterized by the additional step of utilizing said body pursuant to its designed-in requirements.

10. The method of claim 7 further characterized by the additional step of utilizing said body pursuant to its designed-in requirements.

11. A method for producing a body of artistic pattern, or of selectively positioned electrical conductivity or which can be inspected for a physical or chemical property exhibiting a gradient below the body surface, such as occurs in a lay-up of curable plastic composite material and layers of sheet or woven filler material for example, said method comprising the steps of:
(a) forming the body to a desired shape with at least one surface that is configured to a design shape dictated by use requirements of the body,
(b) providing a raised portion or portions on said one surface at a location that is not critical due to such design considerations,
(c) removing said raised portion to provide a visual indication of the property gradient in the scar area of the removed portion.

12. The method of claim 11 further characterized by testing the body for the property and its gradient in the scar area.

13. The method of claim 12 wherein said raised portion has a height above said one surface corresponding to the depth to which said gradient is desired below said surface.

14. A body produced with a physical or chemical property gradient extending inwardly from the body surface according to the method comprising the steps of:
(a) forming the body to a desired shape with several surfaces, some of which are critically contoured as dictated by design requirements, and some of which are non-critical;
(b) providing a raised portion on at least one non-critical surface, and
(c) subjecting the body to a surface treatment process such that at least some of said critical surfaces and at least said one non-critical surface are altered in one or more of the properties, whereby said raised portion is available for testing the property gradient.

15. A body produced according to the method of claim 14 wherein the step of providing a raised portion on said non-critical surface, more particularly comprises shaping said raised portion so that it has different sections at different heights above the non-critical surface.

16. A body produced according to the method of claim 15 including the further step of removing said raised portion after subjecting the body to a surface treatment.

17. A body produced according to the method of claim 14 including the further step of removing at least some of said raised portion after subjecting the body to surface treatment.

18. A body produced according to the method of claim 14 wherein the step of providing a raised portion comprises providing a raised portion having a height above the non-critical surface at least equal to the desired depth of the property gradient.

* * * * *